United States Patent [19]

Banasiak

[11] 4,331,559

[45] May 25, 1982

[54] OLEFIN DISPROPORTIONATION

[75] Inventor: Dennis S. Banasiak, Bartlesville, Okla.

[73] Assignee: Phillips Petroleum Company, Bartlesville, Okla.

[21] Appl. No.: 230,982

[22] Filed: Feb. 3, 1981

Related U.S. Application Data

[62] Division of Ser. No. 101,031, Dec. 6, 1979, Pat. No. 4,269,780.

[51] Int. Cl.$^3$ .............................................. B01J 31/12
[52] U.S. Cl. ............................................... 252/429 R
[58] Field of Search ................................... 252/429 R

[56] References Cited

U.S. PATENT DOCUMENTS

| | | | |
|---|---|---|---|
| 3,637,893 | 1/1972 | Singleton | 260/683 D |
| 3,689,433 | 9/1972 | Kroll | 252/429 R |
| 3,723,563 | 3/1973 | Bradshaw | 260/683 D |
| 3,761,537 | 9/1973 | Homeier | 260/683 D |
| 3,974,196 | 8/1976 | Nakamula | 260/410.9 R |
| 4,005,047 | 1/1977 | Chauvin et al. | 252/429 R |
| 4,088,672 | 5/1978 | Waddan | 260/465.8 R |
| 4,247,417 | 1/1981 | Banasiak | 252/429 R |
| 4,248,738 | 2/1981 | Banasiak | 252/429 R |
| 4,250,063 | 2/1981 | Kotani et al. | 252/429 R X |

FOREIGN PATENT DOCUMENTS 773544 4/1972 Belgium .......................... 252/429 R

OTHER PUBLICATIONS

Y. Chauvin et al., "Proceedings of Metathesis Symposium", (1976), pp. 116-124.
Chem. Absts. 86: 71636y, (1977).
Chem. Absts. 82: 124822g, (1975).
Chem. Absts. 85: 178044k, (1976).

Primary Examiner—Patrick Garvin

[57] ABSTRACT

A process for forming non-polymeric disproportionation products of non-conjugated olefins using catalysts comprising (1) at least one of certain neutral carbene complexes, and (2) at least one of certain compounds of Groups IVa, IVb, Vb, VIb, VIIb, VIII, and Ib of the Periodic Table of the Elements.

10 Claims, No Drawings

OLEFIN DISPROPORTIONATION

This application is a divisional of copending application Ser. No. 101,031, filed Dec. 6, 1979, now U.S. Pat. No. 4,269,780.

This invention relates to the disproportionation of olefins. More specifically, this invention relates to a novel catalyst system and a novel process for the disproportionation of olefins.

The disproportionation or metathesis of olefins is a reaction in which one or more olefinic compounds are transformed into other olefins of different molecular weights. The disproportionation of an olefin to produce one olefin of a higher molecular weight and one olefin of a lower molecular weight can also be referred to as a self-disproportionation. For example, propane can be disproportionated to ethylene and cis- and trans-2-butene. Another type of disproportionation involves the codisproportionation of two different olefins to form still other olefins. For example, the reaction of one molecule of 2-butene with one molecule of 3-hexene can produce two molecules of 2-pentene.

An especially valuable type of disproportionation involves the disproportionation of olefins bearing functional groups such as esters, ethers, chlorides, and the like. For example, 4-penten-1-yl acetate can be disproportionated to ethylene and cis- and trans-1,8-diacetoxy-4-octene. Likewise, 5-chloro-1-pentene can be disproportionated to ethylene and cis-and trans-1,8-dichloro-4-octene. The products bearing functional groups are valuable for use in polymer formation and chemical transformation to yield industrially valuable products. The term functional olefins is used herein to denote those olefins containing functionality other than hydrocarbyl olefinic unsaturation.

Several catalyst systems have been proposed for the disproportionation of olefins. Several disadvantages have been observed for these catalyt systems. In some cases, isomerization of the double bond of the starting material or product occurs and disproportionation involving the isomeric olefins yields a mixture of products which is difficult to separate. With certain catalysts, polymerization of the olefins occurs at long reaction times or high reaction temperatures. Some catalyts cause alkylation of aromatic solvents with the olefin, thereby consuming some of the reactant or product and producing a more complex product mixture. Some catalysts are only effective for terminal olefins and other catalysts may be effective only with internal olefins. Many of the metathesis catalyst systems use organoaluminum compounds which are expensive and present operational difficulties during production, storage, and use.

An object of the present invention is to provide a novel disproportionation catalyst which produces very little undesirable olefin isomerization and which does not require the employment of expensive organoaluminum components.

Another object of the present invention is to provide a process for reacting olefins to obtain non-polymeric disproportionation products. The term non-polymeric disproportionation products as used herein is intended to denote those products having molecular weights no greater than that of the sum of the molecular weights of four of the olefinic reactants.

Other objects, features and advantages of the present invention will appear more fully from the following description.

SUMMARY OF THE INVENTION

In accordance with the present invention, olefins can be disproportionated to non-polymeric products using a novel homogeneous catalyst system comprising (1) at least one metal compound wherein the metal is selected from Groups IVa, IVb, Vb, VIb, VIIb, VIII, and Ib of the Periodic Table of the Elements as defined in "The Merck Index" 9th. Ed., M. Windholz, Ed., Merck & Co., Rahway, N.J. 1976, inside front cover, and (2) at least one neutral, i.e., non-ionic, carbene complex.

In accordance with certain specific embodiments of the present invention, additional materials are added to the catalyst system to provide improved results. Many of the catalyst systems used in the present invention have the advantage of being effective for disproportionation of both functional and non-functional olefins.

The Catalyst System

Each metal compound component of the basic catalyst system is selected from the group consisting of the chlorides and bromides of the metals of Groups IVa, IVb, Vb, VIb, VIIb, VIII, and Ib; and the oxychlorides and oxybromides of molybdenum, tungsten, vanadium, and chromium; wherein if the metal is vanadium it is in an oxidation state of either 4 or its highest, stable, common, ionic oxidation state; if the metal is molybdenum, tungsten, or rhenium it is in an oxidation state of either 5 or its highest, stable, common, ionic oxidation state; and if the metal is not vanadium, molybdenum, tungsten or rhenium the metal is in its highest, stable, common, ionic, oxidation state.

Suitable metals for use in the present invention include (Group IVa) germanium, tin, lead, (Group IVb) titanium, zirconium, hafnium (Group Vb) vanadium, niobium, tantalum (Group VIb) chromium, molybdenum, tungsten (wolfram), (Group VIIb) manganese, technetium, rhenium, (Group VIII) iron, cobalt, nickel, ruthenium, rhodium, palladium, osmium, iridium, platinum, (Group Ib) copper, silver, and gold.

For reasons of availability and reactivity the currently preferred metals for use in the metal compound component are germanium, tin, titanium, zirconium, vanadium, tantalum, molybdenum, tungsten, rhenium, iron, and copper.

Specific examples of suitable metal compounds include germanium tetrachloride, tin tetrachloride, tin tetrabromide, lead tetrachloride, titanium tetrachloride, titanium tetrabromide, zirconium tetrachloride, hafnium tetrachloride, vanadium tetrachloride, vanadium oxytrichloride, niobium pentachloride, tantalum pentachloride, chromium trichloride, molybdenum pentachloride, molybdenum pentabromide, molybdenum oxytetrachloride, tungsten hexachloride, tungsten pentabromide, tungsten oxytetrachloride, manganese trichloride, rhenium pentachloride, iron trichloride, iron tribromide, cobalt trichloride, nickel(II) bromide, ruthenium trichloride, rhodium trichloride, palladium dichloride, osmium trichloride, iridium tetrachloride, platinum tetrachloride, copper(II) chloride, copper(II) bromide, silver chloride, and gold(III) chloride. Mixtures of these metal compounds can be used if desired. An especially valuable mixture of metal compounds is tin tetrachloride and germanium tetrachloride which results in a higher yield than would be expected by the results of the individual halides.

The carbene complex components of the catalyst systems employed in this invention are selected from neutral or non-ionic carbene complexes which can be represented by the general formula

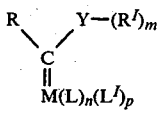

wherein R is selected from the group consisting of alkyl or cycloalkyl radicals containing 1 to 10 carbon atoms per radical, aryl or substituted aryl radicals containing 6 to 30 carbon atoms per radical wherein the substituted aryl radicals can have one or more substituents each of which can be the same or different and selected from the group consisting of halides, alkoxides, and alkyl radicals containing 1 to 20 carbon atoms per radical; wherein $R^I$ is selected from the group consisting of alkyl, cycloalkyl, aryl, substituted aryl, triarylsilyl, and trialkylsilyl radicals containing 1 to 30 carbon atoms per radical and wherein the aryl substituents are as described for R; M can be Cr, when said metal compound component contains Ti, or M can be W or Re; Y is O, Se, S, N, or P, each L is a neutral ligand individually selected from CO, NO, $PR_3^I$, $PCl_3$, $PF_3$, and pyridine, where $R^I$ is as defined above, and $L^I$ is cyclopentadienyl; p is 0 or 1; n is 5 when p is 0 or 2 when p is 1; and m is 2 when Y is n or P and 1 when Y is O, Se, or S.

The particular carbene complex needed to provide an active catalyst component is in some cases dependent on the other components of the catalyst system. Some of those situations have been covered in the description set forth in the preceding paragraph. In addition, it should be noted that R and $R^I$ should not both be aryl or substituted aryl if Y is S unless the catalyst system is as described for embodiment A below. R should not be alkyl or cycloalkyl unless (1) the metal compound component contains Ti or W or (2) the catalyst system is as described for embodiments A, B, C, and D below and non-functional olefin are used as reactants.

For reasons of high reactivity, the currently preferred carbene complexes for use in the present invention are represented by the general formula I wherein R is an aryl radical containing from 6 to 12 carbon atoms per radical or, when the metal halide component contains titanium, an alkyl radical containing 1 to 10 carbon atoms per radical, $R^I$ is an alkyl radical containing from 1 to 10 carbon atoms per radical, Y is O or S with the limitation that Y is not S when the metal compound is Ti, m is 1, M is tungsten, L is CO, n=5, and p=0.

For reasons of ease of preparation and high reactivity, the currently most preferred carbene complex is (methoxyphenylcarbene)pentacarbonyltungsten(O) which can be represented by the following formula II:

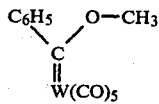

wherein $C_6H_5$ is a phenyl group.

The carbene complexes can be prepared by any of several published procedures, viz., D. J. Cardin et al, Chem. Rev., 72 545 (1972), D. J. Cardin et al, Chem. Soc. Rev., 2, 99 (1973), C. P. Casey, in "Transition Metal Organometallic in Organic Synthesis", Vol. 1, H. Alper, Ed., Academic Press, 1976, pp. 189–233; and "Inorganic Synthesis" Vol. 17, 95–99 (1979). In a typical preparation, carbene complex II is prepared by reacting tungsten hexacarbonyl with phenyllithium and then with trimethyloxonium tetrafluoroborate.

Specific examples of neutral carbene complexes include (methoxyphenylcarbene)pentacarbonyltungsten(O), (p-chlorophenylmethoxycarbene)pentacarbonyltungsten(O), (p-methylphenylmethoxycarbene)pentacarbonyltungsten(O), (p-methoxyphenylmethoxycarbene)pentacarbonyltungsten(O), (phenoxyphenylcarbene)pentacarbonyltungsten(O), (cyclohexyloxyphenylcarbene)pentacarbonyltungsten(O), (butoxyphenylcarbene)pentacarbonyltungsten(O), (octyloxyphenylcarbene)pentacarbonyltungsten(O), (hexadecyloxyphenylcarbene)pentacarbonyltungsten(O), (eicosyloxyphenylcarbene)pentacarbonyltungsten(O), (phenyltrimethylsilyloxycarbene)pentacarbonyltungsten(O), (phenyltriphenylsilyloxycarbene)pentacarbonyltungsten(O), (methylthiophenylcarbene)pentacarbonyltungsten(O), (dimethylaminophenylcarbene)pentacarbonyltungsten(O), (methoxyphenylcarbene)pentanitrosyltungsten(O), (methoxyphenylcarbene) $\eta^5$-cyclopentadienyldicarbonyl rhenium(1), (methoxyphenylcarbene)tetracarbonyl(triphenylphosphine)tungsten(O), and (methoxyphenylcarbene)pentacarbonylchromium(O). Mixtures of carbene complexes can be used if desired.

The ratio of the catalyst components can be expressed in terms of a molar ratio of metal compound to carbene complex. The molar ratio of the metal compound to the carbene complex in the present invention for Group IVa metal compounds is broadly from about 1/1 to about 500/1 and preferably from about 5/1 to about 100/1. For the metal compounds of Groups IVb, VIb, VIIb, and VIII, the molar ratio of metal compound to carbene complex is broadly from about 0.1/1 to about 50/1 and preferably from about 0.5/1 to about 20/1.

For Group Vb and Ib metals, such as vanadium and copper, the molar ratio of metal compound to carbene complex is broadly from about 0.1/1 to about 8/1 and preferably from about 0.5/1 to about 5/1. At molar ratios lower than the lower limits, the disproportionation reaction is unacceptably slow while molar ratios above the upper limits result in no improvement or are detrimental to the reaction.

As mentioned above, the present invention also includes alternate embodiments wherein additional materials are employed in the catalyst system.

EMBODIMENT A

When the metal compound component comprises germanium, tin, or lead tetrahalide, advantages are obtained by including a silicon tetrahalide when in the carbene complex R is selected from a group consisting of alkyl, cycloalkyl, aryl, or substituted aryl radicals containing from 1 to about 30 carbon atoms per radical and the aryl substituents being one or more or a mixture selected from a group consisting of halides and alkoxides or alkyl radicals containing 1 to 20 carbon atoms per radical, and the like, with the limitation that R should not be alkyl or cycloalkyl when a functional olefin is used, $R^I$ is selected from a group consisting of alkyl, cycloalkyl, aryl, substituted aryl, trialkylsilyl, or triarylsilyl radicals containing from 1 to 30 carbon atoms per radical with the aryl substituents being the same as described above for R with the limitation that R and $R^I$ are not both aryl or substituted aryl when Y is S and functional olefins are used, Y is O or S, m is 1, M is tungsten or rhenium, L is CO or NO, p is 0 when n is 5 or p is 1 and n is 2, and $L^I$ is cyclopentadienyl.

The germanium, tin, and lead tetrahalides employed in embodiment A are selected from the group consisting of tin tetrachloride, tin tetrabromide, germanium tetrachloride, germanium tetrabromide, lead tetrachloride, and lead tetrabromide. For reasons of high reactivity, the presently preferred metal compound components are tin tetrachloride and germanium tetrachloride.

The silicon tetrahalide is selected from silicon tetrachloride and silicon tetrabromide.

The molar ratio of the germanium, tin, or lead tetrahalide to the carbene complex in this embodiment is broadly from about 1/1 to about 500/1 and preferably from about 5/1 to about 100/1. The molar ratio of silicon tetrahalide to the germanium, tin, or tetrahalide is broadly from about 0.1/1 to about 200/1 and preferably about 0.5/1 to about 50/1.

EMBODIMENT B

When the metal compound component comprises tin tetrahalide, zirconium tetrahalide, tungsten hexahalide, tungsten pentahalide, or a tungsten oxyhalide, advantages can be obtained by including a tetraorganogermanium when the carbene complex is as described in embodiment A.

The metal compound components in this embodiment are selected from the group consisting of tin tetrachloride, tin tetrabromide, zirconium tetrachloride, zirconium tetrabromide, tungsten hexachloride, tungsten hexabromide, tungsten pentachloride, tungsten oxytetrabromide, tungsten oxytetrabromide, and tungsten pentabromide. For reasons of economics and reactivity, the presently preferred components are tin tetrachloride, zirconium tetrachloride, and tungsten hexachloride.

The tetraorganogermanium employed in this embodiment is selected from those having the formula $GeR^{II}_4$ wherein $R^{II}$ is an alkyl, aryl, or alkaryl radical containing from 1 to about 10 carbon atoms per radical. Examples of suitable tetraorganogermaniums include tetramethylgermanium, tetraethylgermanium, tetrapropylgermanium, tetrabutylgermanium, tetraoctylgermanium, tetradecylgermanium, tetraphenylgermanium, tetra-p-tolygermanium, dimethyldiphenylgermanium, and the like.

The molar ratio of the tin tetrahalide to the carbene complex in this embodiment is broadly from about 1/1 to about 500/1 and preferably from about 5/1 to about 100/1. The molar ratio of the zirconium or tungsten halides, or tungsten oxyhalides to the carbene complex is broadly from about 0.1/1 to about 50/1 and preferably from about 0.5/1 to about 20/1. The molar ratio of the tetraorganogermanium to the tin, zirconium, or tungsten halides or tungsten oxyhalides is broadly from about 0.1/1 to about 100/1 and preferably from about 0.5/1 to about 50/1.

EMBODIMENT C

When the metal compound component comprises a Group IVa metal tetrahalide advantages are provided by including carbon tetrachloride when the carbene complex is as described for embodiment A. In view of their high reactivity the currently preferred metal components for this embodiment are lead tetrachloride, germanium tetrachloride, and tin tetrachloride.

The molar ratio of the Group IVa tetrahalide to the carbene complex is broadly from about 1/1 to about 500/1 and preferably from about 5/1 to about 100/1. The molar ratio of carbon tetrachloride to the Group IVa tetrahalide is broadly from about 0.1/1 to about 200/1 and preferably from about 0.5/1 to about 50/1.

An invention closely related to embodiment C involves substituting silicon tetrachloride for at least part of the Group IVa metal tetrahalides.

EMBODIMENT D

When the metal compound component comprises zirconium tetrachloride or tetrabromide advantages are obtained by including a tetraorganotin compound of the formula $SnR^{II}_4$ wherein $R^{II}$ is as described above in the discussion of embodiment B when the carbene complex is as described for embodiment A.

Examples of suitable tetraorganotin compounds include tetramethyltin, tetraethyltin, tetrapropyltin, tetrabutyltin, tetrahexyltin, dimethyldiphenyltin, tetraoctyltin, tetradecyltin, tetraphenyltin, tetra-p-tolyltin and the like.

The molar ratio of the zirconium halide to the carbene complex is broadly from about 0.1/1 to about 50/1 and preferably from about 0.5/1 to about 20/1. The molar ratio of the tetraorganotin to the zirconium halide is broadly from about 0.1/1 to about 200/1 and preferably from about 0.5/1 to about 50/1.

OLEFIN REACTANTS

Suitable olefin reactants can be readily discovered by routine experimentation. Generally the process involves the contacting of two olefinic reactants, which may be the same or different olefins, with a catalyst system of the type described above. Typically, at least one of the olefinic reactants contains 3 to 30 carbon atoms per molecule and one or more non-conjugated carbon-carbon double bonds.

Generally, at least one of the olefinic reactants contains one or two non-conjugated carbon-carbon double bonds and is an acyclic olefin represented by the formula:

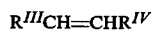

$$R^{III}CH=CHR^{IV}$$

wherein $R^{III}$ and $R^{IV}$ are independently selected from a group consisting of hydrogen, alkyl radicals, alkaryl radicals, and alkenyl radicals with each of the radicals containing from 1 to about 18 carbon atoms per radical or a monocyclic olefin represented by the formula:

wherein $R^V$ is an alkylene or alkenylene radical containing from 5 to about 16 carbon atoms and wherein each of the radicals $R^{III}$, $R^{IV}$, and $R^V$ can contain one or more or a mixture of functional groups selected from a group consisting of esters, ethers, halides, e.g., fluorine, chlorine, bromine, or iodine, trisubstituted silyloxy($-OSiR^{VI}_3$), trisubstituted silyl($-SiR^{VI}_3$), and ammonium salts ($-N^+R^{VII}_3x^-$) wherein $R^{VI}$ is an alkyl, aryl, or substituted aryl radical containing from 1 to about 20 carbon atoms per radical with the aryl substituents being halides, alkoxides, or alkyl radicals, each $R^{VII}$ is hydrogen or an alkyl radical with at least one alkyl radical being required and containing from 1 to 10 carbon atoms per radical, and X is chloride, bromide, or iodide.

The first four of these functional groups, i.e., esters, ethers, halides, and trisubstituted silyloxy, must be located at least two saturated carbon atoms from the olefinic carbons, i.e., the functional group is on a carbon atom that is separated from the olefinic carbons by at least one saturated carbon atom. The last two functional groups must be located at least one carbon atom from the olefinic carbons.

The olefinic double bond in an unsaturated ester can be located on either the alcohol or on the acid portion from which the ester was formally prepared. When an aryl group is present in the olefin, the aryl and olefinic groups should not be conjugated.

Examples of suitable acyclic olefinic reactants include propene, 1-butene, 1-pentene, 2-pentene, 1-hexene, 2-hexene, 1-octene, 2-octene, 4-methyl-1-heptene, 1-decene, 2-decene, 6-dodecene, 1-tetracene, 1-eicosene, 1,4-hexadiene, 4-phenyl-1-butene, 4-phenyl-1-octene, 4-pentene-1-yl acetate, 4-chloro-1-pentene, 5-chloro-1-pentene, methyl oleate, methyl 10-undecenoate, ethyl oleyl ether, 3-butenyl methyl ether, 3-pentenyl propyl ether, methyl 4-hexenoate, ethyl 5-hexenoate, 4-bromo-1-butene, 4-iodo-1-butene, 3-buten-1-oxytrimethylsilane, 3-propen-1-yltrimethylsilane, and 3-butene-1-yltrimethylammonium chloride. Examples of suitable monocyclic olefins include cycloheptene, cyclooctene, cyclononene, cyclotetradecene, 4-chloro-1-cyclooctene, 1,5-cyclododecadiene, and 1,6-cyclodecadiene.

When two different olefinic reactants are utilized in the disproportionation, one of the olefins must be an olefin as described above and the other olefin can be either another olefin as described above or can be ethylene, a monocyclic monoolefin containing 4, 5, or 6 carbons in the ring, e.g., cyclobutene, cyclopentene, cyclohexene, or polycyclic mono- or diolefins. Examples of suitable polycyclic olefins include bicyclo[2.2.2]oct-2-ene, bicyclo[2.2.2]oct-2,5-diene, bicyclo[2.2.1]hept-2-ene, and bicyclo[3.3.0]oct-2-ene.

When two different olefinic reactants are employed in the disproportionation process, the molar ratio of one olefinic reactant to the other olefinic reactant is not critical, and, although about equimolar quantities are normally employed, up to as much as a 10-fold excess, preferably up to a 2-fold excess of one olefinic reactant can be employed.

Generally, all the above-described catalyst systems are considered suitable for the disproportionation of non-functional olefins and halogenated olefins wherein the halogens are located at least two carbons from the olefinic carbons. For disproportionations involving olefins containing functional groups other than halogens, it appears that the metal compound component must be a chloride or oxychloride. Titanium tetrachloride appears to be inactive with certain functional olefins such as acetates.

The catalyst system of embodiment A is in addition useful for the disproportionation of the other of the above-recited functional olefins, i.e., those containing esters, ethers, trisubstituted silyloxy, trisubstituted silyl, and ammonium salts.

REACTION CONDITIONS

The amount of catalyst employed in the process of this invention can be expressed in terms of the molar ratio of olefin to carbene complex component. Generally, the molar ratio of the total stoichiometric amount of olefinic reactant to carbene complex component is in the range of about 1/1 to about 500/1 and preferably from about 50/1 to about 2000/1. The term "total stoichiometric amount" is used herein to denote the moles of reactant that could theoretically react so as to distinguish from cases when two or more olefins are employed and one or more is used in a greater amount than will react. Thus, the amount of catalyst is generally based upon the amount of reactive olefins and not on excess olefin.

The disproportionation reaction of this invention can be carried out at temperatures between about 35° C. and about 200° C. While lower temperatures can be used, the reaction rates are generally too low to be of interest. Temperatures above 200° C. can be used, but excess decomposition of the reaction components can occur. The preferred reaction temperatures are from about 50° C. to about 125° C.

The pressure during the disproportionation reaction can be from about atmospheric to about 5000 psig (34470 kiloPascals kPa). Preferably, the pressure is from about atmospheric to about 1000 psig (6894 kPa).

The disproportionation reaction can be carried out in the presence of diluents such as saturated hydrocarbons, e.g., hexane, octane, cyclohexane, aromatic hydrocarbons, e.g., benzene, toluene, or halogenated compounds, e.g., chlorobenzene, chloroform, methylene chloride, bromoform, and the like.

Diluents containing aromatic groups, e.g., chlorobenzene, have been found to sometimes undergo alkylation when utilized with Group VIb metal halides, e.g., $WCl_6$, at the higher metal compound component levels. This can of course result in decreased yields and therefore may be viewed as undesirable. Also the use of saturated hydrocarbons, e.g., hexane, as diluents with catalyst systems containing metal compounds from Group Vb frequently results in decreased yields and are thus less desirable. This indicates that the diluent is not a completely inert component of the reaction system and attention must be paid to the diluent used for any specific combination of reaction ingredients. In embodiment C, the carbon tetrachloride component of the catalyst system can be used, especially in the upper portion of the concentration range, as a diluent.

The amount of diluent can be expressed as a volume ratio of diluent to the olefin. Suitable volume ratios of diluent to olefin can be from about 0/1 to about 500/1 and preferably from about 1/1 to about 300/1.

The presence of oxygen and water has been found to be deleterious to the disproportionation reaction and should be substantially avoided during the reaction. Inert gases such as nitrogen or helium can be used to maintain a dry, inert atmosphere during the reaction.

The metal compounds used as components of the catalyst system should be pure, free of oxygen or water, and free of any hydrolysis products. In general, the yield of disproportionation product decreases as the metal compound purity decreases.

The functional olefins used in the disproportionation reaction should be dry and free of polar materials such as carboxylic acids or alcohols. A purification step to remove impurities by such methods as filtering through silica gel and storing over molecular sieves or distilling from suitable drying agents is beneficial.

The reaction time period depends on the reaction temperature and pressure as well as on the nature of the particular catalyst system and olefinic reactant used. The reaction time is generally from about 30 minutes to 14 days. Preferably the reaction time is from about 2 to about 120 hours. Olefins containing functional groups frequently undergo disproportionation reactions slower than non-functional olefins and longer reaction times may be appropriate.

REACTION PRODUCT WORKUP

The reaction product mixture from the disproportionation can be worked up using any combination of conventional separation and purification techniques. Depending on the relative volatilities of the unreacted starting olefins, the olefin products and the diluent, the reaction mixture can frequently be separated by fractional distillation. The unreacted starting olefin and diluent can be recycled to the reaction zone if desired. The olefin products can be purified by conventional techniques such as crystallization, distillation, or extractions.

The carbene catalyst can be removed, if desired, by the addition of dilute aqueous ammonia to decompose and precipitate the catalyst, followed by filtration and extraction. The resultant organic layer can then be worked up in a conventional manner.

REACTION PRODUCTS

According to the process of this invention, two olefinic reactants are disproportionated to form a product containing one or two olefins having a total number of carbon atoms equal to the sum of the carbon atoms of the two olefinic reactants and having a number of ethylenic double bonds equal to the sum of the ethylenic double bonds of the reactants.

One variation of the process comprises the disproportionation of two molecules of the same olefinic reactant. The reaction of two molecules of an acyclic olefin of formula VI generally produces one olefin of a higher carbon number and one olefin of a lower carbon number as depicted in equation (1)

$$2R^{III}CH=CHR^{IV} \rightarrow R^{III}CH=CHR^{III} + R^{IV}CH=CHR^{IV} \quad (1)$$

wherein $R^{III}$ and $R^{IV}$ have the previously stated significance. If $R^{III}$ and $R^{IV}$ represent identical groups, it is appreciated that the disproportionation reaction will not cause any skeletal changes as the products $R^{III}CH=CHR^{III}$ and $R^{IV}CH=CHR^{IV}$ will be equivalent to $R^{IV}CH=CHR^{III}$. By way of specific illustration, the reaction of two molecules of propylene produces ethylene and 2-butene. However, the reaction of two molecules of 2-butene produces two molecules of 2-butene. Where $R^{III}$ and $R^{IV}$ are combined to form a cyclic olefin, the reaction of two molecules of the cyclic olefin produces a single cyclic diolefin. At high dilution, the cyclic diolefin can be isolated, but in more concentrated solutions, further disproportionation frequently occurs to form materials of higher molecular weight. By way of specific illustration, the reaction of two molecules of cyclooctene in a dilute reaction mixture produces 1,9-cyclohexadecadiene.

Generally, when the disproportionation product contains an internal (non-terminal) double bond, a mixture of cis- and trans-isomers are present. For convenience, only one isomer is shown in the products below.

Another variation of the process comprises the disproportionation of two different acyclic olefinic reactants. By way of specific illustration, the reaction of 2-butene and 3-hexene produces two molecules of 2-pentene.

Still another variation of the process is "ring-opening" disproportionation wherein an acyclic olefinic reactant is contacted with a cyclic olefinic reactant. The product of "ring-opening" is a single olefinic compound with one less carbocyclic ring than the cyclic olefinic reactant, e.g.,

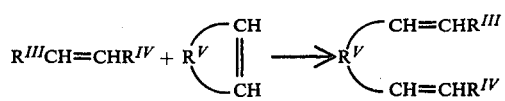

wherein $R^{III}$, $R^{IV}$, $R^{V}$ are as previously defined. By way of specific illustration, from reaction of 2-butene and cyclopentene is produced 2,7-nonadiene. Other typical products include 2,8-decadiene produced by reaction of cyclohexene and 2-butene, 3,8-undecadiene produced from 3-hexene and cyclopentene, 1,5,9-decatriene produced by reaction of ethylene and 1,5-cyclooctadiene, and 1,4-divinylcyclohexane from ethylene and bicyclo[2.2.2]oct-2-ene.

Olefins containing functional groups undergo disproportionation in a similar manner. For example, 4-penten-1-yl acetate yields a cis- and trans-mixture of 1,8-diacetoxy-4-octene and ethylene (equation 2)

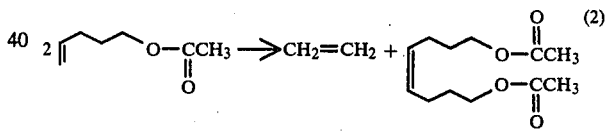

Methyl oleate disproportionates to cis- and trans-9-octadecene and a cis- and trans- mixture of dimethyl 9-octadecen-1,18-dioate (equation 3).

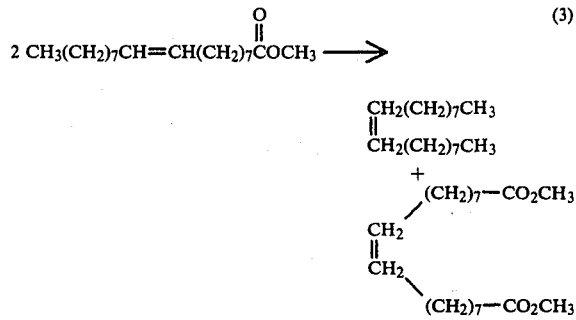

The co-disproportionation of cyclopentene with 4-penten-1-yl acetate yields a mixture of the co-disproportionation product 4,9-decadien-1-yl acetate and the self-disproportionation product from the 4-penten-1-yl acetate (both products contain cis- and trans- isomers).

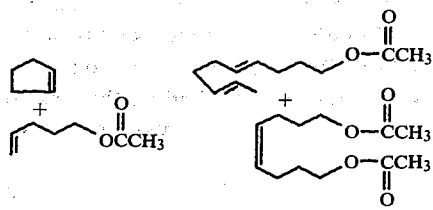

Some secondary disproportionation reactions between products and reactants are also frequently observed.

PRODUCT UTILITY

The olefinic products, for the most part, have established utility as precursors of polymers, e.g., as the third component of ethylene-propylene terpolymers useful as synthetic elastomers. When functional groups are present on the olefinic product, the resulting polymer will contain functional groups which can be used to crosslink the polymer.

The olefinic products are converted to secondary and tertiary alcohols as by sulfuric acid-catalyzed hydration. Alternatively, the olefinic products are converted by conventional "Oxo" processes to aldehydes which are hydrogenated with conventional catalysts to the corresponding alcohols. The $C_{12}$–$C_{20}$ alcohols thereby produced are ethoxylated as by reaction with ethylene oxide in the presence of a basic catalyst, e.g., sodium hydroxide, to form conventional detergents and the lower molecular weight alcohols are esterified by reaction with polybasic acids, e.g., phthalic acid, to form plasticizers for polyvinyl chloride.

Olefinic products containing functional groups are useful as perfumes as well as for intermediates for the preparation of drugs and bioactive substances of insects.

EXAMPLES

The non-functional and functional olefins used in the following examples were commercial materials which were usually distilled, contacted with silica gel, and stored over 4 A molecular sieves. Diluents were usually distilled from the appropriate drying agent and stored over 4 A molecular sieves. The various metal halides and organometallics were commercial materials which were normally used without further purification, but with careful exclusion of moisture and oxygen. In several cases, fresh reagents were found to give better disproportionation results than older reagents which are believed to have changed in chemical composition, for example by hydrolysis during aging. During the reaction evaluations, it was found that the careful exclusion of oxygen and moisture from the reaction system was extremely important for successful disproportionation results.

The carbene complexes were prepared by published procedures. Typically, they were prepared by reacting the appropriate metal carbonyl with an organolithium and then adding a trialkyloxonium tetrafluoroborate. For example, tungsten hexacarbonyl was reacted with phenyllithium and was then reacted with trimethyloxonium tetrafluoroborate to form (methoxyphenylcarbene)pentacarbonyltungsten(O)

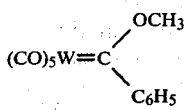

The introduction of alkylthio- or arylthio- groups was accomplished by reacting the corresponding alkoxy carbene complex with the appropriate thioalcohol, e.g.,

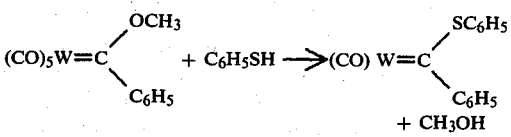

Trialkylsilyloxy groups were introduced by the reaction of the metal carbonyl with an organolithium, the addition of tetramethylammonium bromide, and reaction with a chlorotrialkylsilane. See E. O. Fischer et al, Chem. Ber., 110, 2575–2583, 1977. (Methoxyphenylcarbene)tetracarbonyl(triphenylphosphine)tungsten(O) was prepared by refluxing (methoxyphenylcarbonyl)pentacarbonyltungsten(O) with triphenylphosphine. The carbene complexes were stored in a desiccator in a freezer before use in a reaction.

Each of the runs in the following examples was carried out in a 10 oz. or 32 oz. beverage bottle equipped with a magnetic stirrer, a self-sealing elastomeric cap liner, and a three-hole crown cap. The liquid reaction components were charged to the dried, nitrogen flushed bottle by syringe through the cap. Solids were added to the bottle before attaching the cap. The reaction mixture was heated to the desired temperature and stirred at the reaction temperature for the desired time period. At the conclusion of the reaction time period, the reaction mixture was analyzed by gas-liquid chromatography (glc). The glc peak areas were converted to weights using an internal standard. The disproportionation results are reported as a mole percent based on the conversion desired or accomplished. For example, since 2 molecules of 1-pentene are disproportionated to 1 molecule of ethylene and 1 molecule of 4-octene, the yields of 4-octene are expressed as a mole percent yield based on one half of the number of moles of 1-pentene charged to the reactor. The ethylene product was not determined and the 4-octene is a mixture of cis- and trans-isomers.

Reaction products containing internal double bonds were normally formed as a cis- and trans- mixture and, for simplicity, are not named cis- and trans-. The reaction products were identified in some instances by gas chromatograph/mass spectra and comparison of glc retention times with known materials. In many instances, the products were isolated from the reaction mixture and identified by elemental analysis, infrared spectra, nuclear magnetic resonance spectra, and mass spectra. The product isolation was carried out by diluting the reaction mixture with additional diluent, adding 10% aqueous ammonium hydroxide to precipitate the metal complexes, and filtering. The resulting filtrate was then processed by conventional techniques such as distillation or crystallization to yield the purified products.

EXAMPLE I

Several control runs were carried out to demonstrate that the carbene complexes alone or the metal halides alone are not effective disproportionation catalysts. In run 1, 1.54 g (22 mmoles) of 1-pentene and 4.4 ml of a solution of (methoxyphenylcarbene)pentacarbonyltungsten(O) (0.11 moles) in chlorobenzene was charged to the reaction bottle. The mixture was stirred at room temperature (about 24° C.) for 24 hours. A glc analysis indicated that no reaction had occurred. The mixture was heated to 130° C. and stirred for 48 hours. Another glc analysis of the reaction mixture showed that no reaction had occurred.

In run 2, 1.54 g (22 mmoles) of 1-pentene, 4.4 ml of a solution of (methoxyphenylcarbene)pentacarbonyltungsten(O) (0.22 mmoles) in hexane, and 10 ml of hexane were charged to the reaction bottle. The reaction mixture was stirred at 55° C. for 4 days. A glc analysis of the reaction mixture showed that no reaction had occurred.

In run 3, 1.54 g (22 mmoles) of cis-2-pentene, 4.4 ml of a solution of (methoxyphenylcarbene)pentacarbonyltungsten(O) (0.11 mmoles) in chlorobenzene, and 2 ml of chlorobenzene were charged to the reaction bottle. The reaction mixture was stirred at 140° C. for 20 hours. A glc analysis indicated that no reaction had occurred.

Two runs were carried out using tungsten hexachloride ($WCl_6$) and two different diluents. In each run, the reactor was charged with 1.54 g (22 mmoles) of 1-pentene, 0.22 mmoles of $WCl_6$, in run 4, 10 ml of hexane and in run 5 14.4 ml of chlorobenzene. The mixtures were stirred at 55° C. for 20 hours (run 4) and 48 hours (run 5). The glc analysis indicated that no reaction had occurred in either run.

In run 6, the reaction bottle was charged with 22 mmoles of 1-pentene, 3 mmoles of tin tetrachloride, and 10 ml of chlorobenzene. At the conclusion of a 48 hour time period at 55° C. with stirring, the glc analysis of the reaction mixture showed that no disproportionation had occurred.

The results of these runs show that neutral carbene complexes in the absence of activators are not effective for the disproportionation of olefins and that the metal halides alone are not effective catalysts for the disproportionation of olefins under these reaction conditions.

EXAMPLE II

A series of runs was carried out involving the disproportionation of 1-pentene in the presence of a carbene complex and metal halides from Groups IVa, IVb, and Vb. In each run, the reaction bottle was charged with 22 mmoles of 1-pentene, 0.22 mmoles (0.44 mmoles in run 9) of (methoxyphenylcarbene)pentacarbonyltungsten(O) in 4.4 ml of hexane or chlorobenzene, a metal halide, and additional hexane or chlorobenzene. The reagent quantities, reaction conditions, and the reaction results are presented in Table I.

TABLE I

| Run No. | Metal Halide | mmoles | Group | Diluent, ml | Temp., °C. | Time, Hrs. | 4-Octene Yield % |
|---|---|---|---|---|---|---|---|
| 7 | $SnCl_4$ | 6 | IVa | Hexane 15.4 | 55 | 24 | 52 |
| 8 | $SnCl_4$ | 2 | IVa | Hexane 8 | 55 | 22 | 37 |
| 9 | $SnCl_4$ | 4 | IVa | Hexane 20 | 55 | 96 | 20 |
| 10 | $SnBr_4$ | 2.7 | IVa | Hexane 15 | 55 | 120 | 37 |
| 11 | $GeCl_4$ | 2 | IVa | Hexane 9.4 | 150 | 20 | 10 |
| 12 | $TiCl_4$ | 3 | IVb | Hexane 9.4 | 55 | 20 | 56 |
| 13 | $TiCl_4$ | 6 | IVb | Hexane 14.4 | 55 | 24 | 47 |
| 14 | $TiCl_4$ | 3 | IVb | Hexane 14.4 | 55 | 20 | 40 |
| 15 | $TiCl_4$ | 3 | IVb | Hexane 14.4 | 55 | 72 | 35 |
| 16 | $TiCl_4$ | 3 | IVb | Hexane 14.4 | 59 | 92 | 27 |
| 17 | $TiBr_4$ | 3 | IVb | Hexane 14.4 | 55 | 24 | 5 |
| 18 | $ZrCl_4$ | 2.2 | IVb | Hexane 19.4 | 55 | 20 | 7 |
| 19 | $VCl_4$ | 0.22 | Vb | Hexane 14.4 | 55 | 72 | 30 |
| 20 | $TaCl_5$ | 0.44 | Vb | $C_6H_5Cl$ 14.4 | 55 | 20 | 12 |

The results in Table I demonstrate the process of the present invention for the disproportionation of 1-pentene to 4-octene and ethylene in the presence of Group IVa, IVb, and Vb metal chlorides and bromides and a carbene complex. In a few of these runs (9, 10) at longer reaction times, a small amount of isomerization and halogenation of 1-pentene did occur during the reaction. In some instances, the 4-octene yields varied in repeated runs with the same metal halide, presumably due to further disproportionation at longer reaction times or to variations in catalyst purity.

EXAMPLE III

Another series of runs was carried out involving the process of this invention for the disproportionation of 1-pentene in the presence of a carbene complex and metal compounds from Groups VIb, VIIb, VIII, and Ib. In each run, the reaction bottle was charged with 22 mmoles of 1-pentene, 0.22 mmoles of (methoxyphenylcarbene)pentacarbonyltungsten(O) in 4.4 ml of diluent (hexane or chlorobenzene), a metal halide or a metal oxyhalide, and additional diluent. Each run was carried out at 55° C. The reaction conditions and results are shown in Table II.

TABLE II

| Run No. | Metal Halide | mmoles | Group | Diluent, ml | Time, Hrs. | 4-Octene Yield, % |
|---|---|---|---|---|---|---|
| 21 | $MoCl_5$ | 1 | VIb | $C_6H_5Cl$ 34 | 24 | 42 |
| 22 | $MoCl_5$ | 0.33 | VIb | Hexane 14.4 | 20 | 20 |
| 23 | $MoBr_5$ | 0.44 | VIb | $C_6H_5Cl$ 14.4 | 20 | 3 |
| 24 | $MoOCl_4$ | 0.44 | VIb | Hexane 14.4 | 20 | 31 |
| 25 | $WCl_6$ | 0.22 | VIb | $C_6H_5Cl$ 16.6 | 24 | 19 |
| 26 | $WCl_6$ | 0.22 | VIb | $C_6H_5Cl$ 18.8 | 48 | 16 |
| 27 | $WCl_6$ | 0.22 | VIb | Hexane 14.4 | 20 | 12 |
| 28 | $WBr_5$ | 0.44 | VIb | $C_6H_5Cl$ 14.4 | 48 | 6 |
| 29 | $WOCl_4$ | 0.22 | VIb | Hexane 16.6 | 24 | 3 |

TABLE II-continued

| Run No. | Metal Halide | mmoles | Group | Diluent, ml | Time, Hrs. | 4-Octene Yield, % |
|---|---|---|---|---|---|---|
| 30 | $WOCl_4$ | 0.44 | VIb | Hexane 14.4 | 48 | 15 |
| 31 | $ReCl_5$ | 1 | VIIb | $C_6H_5Cl$ 34 | 96 | 43 |
| 32 | $FeCl_3$ | 0.43 | VIII | Hexane 14.4 | 20 | 26 |
| 33 | $CuCl_2$ | 0.22 | Ib | Hexane 14.4 | 20 | 9 |
| 34 | $CuBr_2$ | 0.44 | Ib | Hexane 14.4 | 72 | 30 |

The results presented in Table II illustrate the process of the present invention for the disproportionation of 1-pentene to 4-octene and ethylene in the presence of a carbene complex and a metal halide from Groups VIb, VIIb, VIII, and Ib or an oxyhalide of molybdenum and tungsten. Small amounts of isomerization and halogenation of the 1-pentene was observed in several of the runs.

EXAMPLE IV

The use of mixtures of metal halides with carbene complexes for olefin disproportionation is illustrated in this example. The reaction bottle in each run was charged with 22 moles of 1-pentene, 0.22 mmoles of (methoxyphenylcarbene)pentacarbonyltungsten(O) in 4.4 ml of hexane, two different metal halides, and an additional quantity of hexane. The reactions were carried out at 55° C. and the results and other ingredient quantities are shown in Table III.

TABLE III

| Run No. | Metal Halide, | mmoles | Metal Halide, | mmoles | Hexane ml | Time, Hrs. | 4-Octene Yield, % |
|---|---|---|---|---|---|---|---|
| 35 | $TiCl_4$ | 3 | $SnCl_4$ | 3 | 12.4 | 20 | 29 |
| 36 | $TiCl_4$ | 3 | $SnCl_4$ | 3 | 17.4 | 20 | 10 |
| 37 | $TiCl_4$ | 3 | $GeCl_4$ | 3 | 14.4 | 72 | 52 |
| 38 | $SnCl_4$ | 3 | $GeCl_4$ | 2 | 12.4 | 20 | 58 |

These results show that mixtures of metal halides can be used with a carbene complex for olefin disproportionation although the yields are sometimes below those obtained by the use of the individual metal halides. However, in run 38 using a combination of $SnCl_4$ and $GeCl_4$, a yield in excess of the expected yield from similar runs with the individual metal halides (see runs 8 and 11 from Table I) was obtained, suggesting a synergistic combination.

EXAMPLE V

Several different olefins were contacted with the catalyst system of the present invention. In each run the olefin, (methoxyphenylcarbene)pentacarbonyltungsten(O), a metal halide, and a diluent were charged to the reaction bottle and the reactions were carried out at 55° C. The quantities utilized and the results of the runs are listed in Table IV.

TABLE IV

| Run No. | Metal Halide, mmoles | | Olefin, mmoles | | Carbene Complex mmoles | Diluent, ml | Time, Hrs. | Product Yield % |
|---|---|---|---|---|---|---|---|---|
| 39 | $SnCl_4$ | 4 | 1-Hexene | 44 | 0.44 | Hexane | 20 | 96 | 30 |
| 40 | $SnCl_4$ | 40 | Cyclooctene | 200 | 2 | Hexane | 310 | 120 | (a) |
| 41 | $WCl_6$ | 2 | cis-2-Pentene | 22 | 0.22 | $C_6H_5Cl$ | 16.6 | 20 | 56 |
| 42 | $WCl_6$ | 1 | 1-Decene | 100 | 1 | $C_6H_5Cl$ | 80 | 288 | 10(b) |
| 43 | $TiCl_4$ | 3 | Isoprene | 22 | 0.22 | Hexane, | 14.4 | 20 | t(c) |
| 44 | $SnCl_4$ | 2 | Styrene | 22 | 0.22 | Hexane | 11.4 | 20 | t(d) |

(a)1,9-Cyclohexadecadiene was isolated and identified, but a yield was not determined.
(b)Isolated yield.
(c)t = trace.
(d)trace of trans-stilbene.

The disproportionations of 1-hexene to 5-decene and ethylene, cyclooctene to 1,9-cyclohexadecadiene, cis-2-pentene to 3-hexene and 2-butene, and 1-decene to 9-octadecene and ethylene (the product yield in Table IV refers to the first product listed when two products are formed) did occur in the presence of the catalyst systems of the present invention. Isoprene (run 43), a conjugated diene and styrene (run 44), which contains an aromatic ring conjugated with the double bond, are not suitable olefins for self-disproportionation with the present catalyst system.

EXAMPLE VI

Several runs were carried out with carbene complexes different than the carbene complex used in previous examples. In each run, 22 mmoles of 1-pentene, a metal halide, 0.22 mmoles of a carbene complex, and from about 9 to about 16 ml of hexane or chlorobenzene were charged to the reaction bottle and the mixture was stirred at 55° C. The ingredients and reaction yields are presented in Table V.

TABLE V

| Run No. | Metal Halide, | mmoles | Carbene Complex | Time, Hrs. | 4-Octene Yield, % |
|---|---|---|---|---|---|
| 45 | $SnCl_4$ | 2.2 | $C_6H_5$\\C=W(CO)$_5$ / $C_2H_5O$ | 18 | 25 |

TABLE V-continued

| Run No. | Metal Halide, | mmoles | Carbene Complex | Time, Hrs. | 4-Octene Yield, % |
|---|---|---|---|---|---|
| 46 | TiCl$_4$ | 3 | C$_6$H$_5$\\C=W(CO)$_5$ / C$_2$H$_5$O | 24 | 31 |
| 47 | SnCl$_4$ | 4.4 | CH$_3$\\C=W(CO)$_5$ / CH$_3$O | 40 | 1 |
| 48 | SnCl$_4$ | 2.2 | CH$_3$(CH$_2$)$_3$\\C=W(CO)$_5$ / CH$_3$O | 120 | 0 |
| 49 | TiCl$_4$ | 3 | CH$_3$\\C=W(CO)$_5$ / CH$_3$O | 19 | 64 |
| 50 | WCl$_6$ | 0.22 | CH$_3$\\C=W(CO)$_5$ / CH$_3$O | 72 | 34 |
| 51 | WCl$_6$ | 0.22 | CH$_3$(CH$_2$)$_3$\\C=W(CO)$_5$ / CH$_3$O | 120 | 45 |
| 52 | TaCl$_5$ | 0.44 | CH$_3$\\C=W(CO)$_5$ / CH$_3$O | 18 | 0 |
| 53 | SnCl$_4$ | 2 | C$_6$H$_5$\\C=W(CO)$_4$ / CH$_3$O  P(C$_6$H$_5$)$_3$ | 72 | 9 |
| 54 | TiCl$_4$ | 2 | C$_6$H$_5$\\C=W(CO)$_5$ / (CH$_3$)$_3$SiO | 96 | 19 |
| 55 | SnCl$_4$ | 3 | C$_6$H$_5$\\C=W(CO)$_5$ / (CH$_3$)$_3$SiO | 96 | 2 |
| 56 | SnCl$_4$ | 3 | CH$_3$\\C=W(CO)$_5$ / C$_6$H$_5$S | 24 | 12 |
| 57 | TiCl$_4$ | 2 | C$_6$H$_5$\\C=Cr(CO)$_5$ / CH$_3$O | 72 | 3 |

(Ethoxyphenylcarbene)pentacarbonyltungsten(O), runs 45 and 46, (methoxyphenylcarbene)tetracarbonyl(triphenylphosphine)tungsten(O), run 53, (phenyltrimethylsilyloxycarbene)pentacarbonyltungsten(O), runs 54 and 55, and (methylthiophenylcarbene)pentacarbonyltungsten(O), run 56, are shown in Table V to be suitable catalyst components for olefin disproportionation. (Methoxymethylcarbene)pentacarbonyltungsten(O) was a suitable catalyst component with titanium and tungsten chlorides (runs 49, and 50) but not with SnCl$_4$ (run 47) or TaCl$_5$ (run 52) (Butylmethoxycarbene)pentacarbonyltungsten(O) was observed to be a suitable catalyst with WCl$_6$ (run 51), but not with SnCl$_4$ (run 48). (Methoxyphenylcarbene)pentacarbonylchromium(O), which has been found to be highly resistant to activation for olefin disproportionation by various materials, was found to form an active catalyst system with TiCl$_4$ (run 57).

EXAMPLE VII

Several runs were carried which show several changes in the components of the catalyst system of this invention which are detrimental to the disproportionation reaction. In each run, 22 mmoles of 1-pentene, 0.11, 0.2, or 0.22 mmoles of a carbene complex or a metal carbonyl, a second component, and 3 to 15 ml of hexane or chlorobenzene were charged to the reaction vessel. The quantities and reaction results are presented in Table VI.

TABLE VI

| Run No. | Metal Halide or Other, mmoles | | Carbene Complex or Metal Carbonyl | Temp., °C. | Time, Hrs. | 4-Octene Yield,[a] % |
|---|---|---|---|---|---|---|
| 58 | CuCl$_2$ | 4.4 | C$_6$H$_5$\C=W(CO)$_5$ / CH$_3$O | 55 | 20 | 0 |
| 59 | CuCl$_2$ · 2H$_2$O | 0.44 | C$_6$H$_5$\C=W(CO)$_5$ / CH$_3$O | 55 | 72 | 0 |
| 60 | ReCl$_3$ | 0.23 | C$_6$H$_5$\C=W(CO)$_5$ / CH$_3$O | 55 | 24 | 0 |
| 61 | VCl$_4$ | 2.2 | C$_6$H$_5$\C=W(CO)$_5$ / CH$_3$O | 55 | 20 | 0 |
| 62 | (CH$_3$CH$_2$)$_3$Al$_2$Cl$_3$, | 2 | C$_6$H$_5$\C=W(CO)$_5$ / CH$_3$O | 55 | 22 | t |
| 63 | AlCl$_3$ | 3 | C$_6$H$_5$\C=W(CO)$_5$ / CH$_3$O | 55 | 20 | 0 |
| 64 | BCl$_3$ | 2 | C$_6$H$_5$\C=W(CO)$_5$ / CH$_3$O | 55 | 22 | 0 |
| 65 | CH$_3$Li | 1.2 | C$_6$H$_5$\C=W(CO)$_5$ / CH$_3$O | 25 | 58 | 0 |
| 66 | I$_2$ | 0.44 | C$_6$H$_5$\C=W(CO)$_5$ / CH$_3$O | 55 | 72 | 0 |
| 67 | SnF$_4$ | 2 | C$_6$H$_5$\C=W(CO)$_5$ / CH$_3$O | 55 | 48 | 0 |
| 68 | SnCl$_4$ | 2 | W(CO)$_6$ | 55 | 24 | 0 |
| 69 | TiCl$_4$ | 3 | W(CO)$_6$ | 55 | 20 | 0 |
| 70 | WCl$_6$ | 0.22 | C$_6$H$_5$\C=Cr(CO)$_5$ / CH$_3$O | 55 | 20 | 0 |
| 71 | SnCl$_4$ | 3 | C$_6$H$_5$\C=Cr(CO)$_5$ / CH$_3$O | 55 | 72 | t |
| 72 | WCl$_6$ | 0.22 | C$_6$H$_5$\C=Mo(CO)$_5$ / CH$_3$O | 55 | 72 | 0 |
| 73 | SnCl$_4$ | 2 | C$_6$H$_5$\C=Mo(CO)$_5$ / CH$_3$O | 55 | 20 | t |
| 74 | TiCl$_4$ | 3 | CH$_3$\C=W(CO)$_5$ / C$_6$H$_5$S | 55 | 48 | 2 |

TABLE VI-continued

| Run No. | Metal Halide or Other, mmoles | Carbene Complex or Metal Carbonyl | Temp., °C. | Time, Hrs. | 4-Octene Yield,[a] % |
|---|---|---|---|---|---|
| 75 | SnCl$_4$ | 2.2 C$_6$H$_5$\\C=W(CO)$_5$/C$_6$H$_5$S | 55 | 72 | 0 |

[a] t = trace

The use of CuCl$_2$ or VCl$_4$ at high levels (mole ratios of metal halide to carbene complex of 10/1 or more) in runs 58 and 61 were found to prevent disproportionation. The use of a metal chloride hydrate (CuCl$_2$.2H$_2$O in run 59) and rhenium in an oxidation state of 3 (run 60) were found to also prevent disproportionation. Several other materials in runs 62 through 67 were substituted for the metal compounds of the present invention and disproportionation did not occur. In runs 68 through 73, the tungsten carbene complex was replaced with W(CO)$_6$ or the corresponding chromium or molybdenum carbene complexes and essentially no disproportionation occurred. The use of a sulfur containing carbene complex with TiCl$_4$ in run 74 resulted in a yield significantly reduced from yields usually obtained with TiCl$_4$ (Table I). (Phenylthiophenylcarbene)pentacarbonyltungsten(O) and SnCl$_4$ did not result in a disproportionation of 1-pentene (run 75).

EXAMPLE VIII

Runs are presented in this example to demonstrate embodiment A of the present invention. In embodiment A, the addition of a silicon tetrahalide to a carbene complex and a germanium, tin, or lead tetrahalide results in a more rapid disproportionation and higher yields. Each run was carried out as in the previous examples with 22 mmoles of 1-pentene and 0.22 mmoles of (methoxyphenylcarbene)pentacarbonyltungsten(O). Runs 76 and 77 were carried out in a chlorobenzene diluent (16.6 ml) at 55° C. Samples were removed at intervals for glc analysis and the results are shown below.

| Time, Hours | Run 76 2.2 mmoles SnCl$_4$ 4-Octene, % | Run 77 2.2 mmoles SnCl$_4$ 3 mmoles SiCl$_4$ 4-Octene, % |
|---|---|---|
| 2 | 3 | 8 |
| 5 | 22 | 22 |
| 7 | — | 36 |
| 8 | 24 | 45 |
| 24 | 35 | 40 |
| 48 | 37 | 34 |

The presence of SiCl$_4$ results in a more rapid conversion and a higher yield of 4-octene.

Runs 78 and 79 were carried out in a mixture of chlorobenzene (14.4 ml) and hexane (2.2 ml) at 55° C. The results are summarized below in terms of the yield of 4-octene at various times during the runs.

| Time, Hours | Run 76 SnCl$_4$ (2.2 mmoles) 4-Octene, % | Run 79 SnCl$_4$ (2.2 mmoles) SiCl$_4$ (3 mmoles) 4-Octene, % |
|---|---|---|
| 2 | trace | — |
| 3 | — | 10 |
| 20 | 35 | 50 |
| 48 | 43 | — |
| 50 | — | 52 |

Again the presence of SiCl$_4$ increases the rate of reaction and yield of 4-octene.

Runs 80 through 83 were carried out in hexane (9 to 16 ml) at 55° C. The following results are expressed in terms of the yields of 4-octene at various times during the runs.

| Time, Hours | Run 80 SnCl$_4$ (2.2 mmoles) 4-Octene, % | Run 81 SnCl$_4$ (2 mmoles) SiCl$_4$ (3 mmoles) 4-Octene, % |
|---|---|---|
| 1 | — | 20 |
| 1.5 | — | 45 |
| 2 | — | — |
| 3.3 | — | 58 |
| 4.3 | — | 70 |
| 5.5 | — | 64 |
| 6 | 9 | — |
| 7 | — | — |
| 8 | — | — |
| 21 | — | 61 |
| 24 | 31 | — |
| 31 | — | — |
| 48 | 65 | — |

| Time, Hours | Run 82 SnCl$_4$ (2.2 mmoles) SiCl$_4$ (3 mmoles) 4-Octene, % | Run 83 SnCl$_4$ (2.2 mmoles) SiCl$_4$ (3 mmoles) 4-Octene, % |
|---|---|---|
| 1 | — | — |
| 1.5 | — | — |
| 2 | 1.6 | — |
| 3.3 | — | — |
| 4.3 | — | — |
| 5.5 | — | — |
| 6 | — | 13 |
| 7 | 26 | — |
| 8 | 39 | — |
| 21 | — | — |
| 31 | 66 | — |
| 48 | 65 | 66 |
| 24 | 62 | 64 |

While the results are variable, perhaps due to variations in reagent purity, the addition of SiCl$_4$ to the basic tin tetrachloridecarbene complex catalyst system results in a faster reaction and in a higher ultimate yield. it is noted in the series of runs with various diluents in this example that hexane has a favorable influence on the product yields when SiCl$_4$ is used.

Several other runs (Table VII) were carried out at 55° C. The disproportionation of 1-pentene does not occur in the absence of the carbene complex (run 84) or in the absence of the SnCl$_4$ (run 85). In addition, the presence of diglyme as a diluent is detrimental to the reaction (run 86). The addition of $SiCl_4$ (run 87) to a catalyst system containing $GeCl_4$ and a carbene complex resulted in an increase in yield containing $GeCl_4$ and a carbene complex resulted in an increase in yield compared with run 11 in Table I.

the mixture was stirred at 55° C. The results are shown in Table VIII.

TABLE VIII

| Run No. | $SnCl_4$, mmoles | $SiCl_4$, mmoles | Carbene Complex Or Metal Carbonyl | Time, Hours | 4-Octene Yield, % |
|---|---|---|---|---|---|
| 88 | 2 | 3 | $CH_3$\\C=W(CO)$_5$ / $CH_3O$ | 48 | 29 |
| 89 | 3 | 6 | $CH_3$\\C=W(CO)$_5$ / $CH_3O$ | 24 | 18 |
| 90 | 2.2 | 2 | $CH_3$\\C=W(CO)$_5$ / $CH_3O$ | 48 | 10 |
| 91 | 2.2 | 3 | $CH_3(CH_2)_3$\\C=W(CO)$_5$ / $CH_3O$ | 120 | 35 |
| 92 | 3 | 3 | $CH_3$\\C=W(CO)$_5$ / $C_6H_5S$ | 48 | 2 |
| 93 | 3 | 3 | $CH_3$\\C=W(CO)$_5$ / $C_6H_5S$ | 24 | 7 |
| 94 | 2.2 | 3 | $C_6H_5$\\C=W(CO)$_5$ / $C_6H_5S$ | 20 | 28 |
| 95 | 2.5 | 3 | $C_6H_5$\\C=W(CO)$_5$ / $(CH_3)_3SiO$ | 96 | 4 |
| 96 | 2 | 3 | $W(CO)_6$ | 48 | 0 |
| 97 | 0.3[a] | 3 | $C_6H_5$\\C=W(CO)$_5$ / $CH_3O$ | 19 | 0 |

[a] $WCl_6$

The results in Table VIII show that a catalyst system containing a carbene complex, $SnCl_4$, and $SiCl_4$ is suitable for olefin disproportionation when alkyl groups (runs 88 to 91), thiophenyl (runs 92 to 94), or trimethyl-

TABLE VII

| Run No. | Metal Halide, mmoles | | Other Halide, mmoles | | Diluent, ml | | Time, Hours | 4-Octene Yield, % |
|---|---|---|---|---|---|---|---|---|
| 84[a] | $SnCl_4$ | 2 | $SiCl_4$ | 3 | Hexane | 5 | 48 | 0 |
| 85[b] | None | | $SiCl_4$ | 20 | Hexane | 8 | 24 | 0 |
| | | | | | Heptane | 11 | | |
| 86[b] | $SnCl_4$ | 2.2 | $SiCl_4$ | 3 | Diglyme | 10 | 72 | 2 |
| | | | | | Hexane | 6.6 | | |
| 87[b] | $GeCl_4$ | 3 | $SiCl_4$ | 3 | Hexane | 9.4 | 20 | 22 |

[a] No carbene complex present.
[b] 0.22 mmoles of (methoxyphenylcarbene)pentacarbonyltungsten(0).

EXAMPLE IX

The use of embodiment A with several different carbene complexes or metal carbonyls for the disproportionation of 1-pentene is illustrated in this example. In each run, the reaction bottle was charged with 22 mmoles of 1-pentene, 0.2 to 0.3 mmoles of the carbene complex or metal carbonyl, $SnCl_4$, $SiCl_4$, and 9 to 18 ml of either hexane or chlorobenzene (runs 94 and 97) and silyloxy groups are present on the carbene carbon. The carbene complexes in runs 88 to 91 were shown previously (Example VI) to be ineffective as catalyst components with $SnCl_4$. Therefore, embodiment A also results in an increase in the range of carbene complexes suitable of olefin disproportionation. Run 96 indicates that $W(CO)_6$ cannot be successfully substituted for the carbene complex. The substitution of $WCl_6$ for the $SnCl_4$ (run 97) results in no disproportionation.

EXAMPLE X

Several more runs were carried out to demonstrate the use of embodiment A of the present invention for the disproportionation of several different olefins. The reaction bottle in each run was charged with the olefin, $SnCl_4$, $SiCl_4$, (methoxyphenylcarbene)pentacarbonyltungsten(O), and either hexane or chlorobenzene. The mixtures were stirred at 55° C. The quantities used and the results are presented in Table IX.

TABLE IX

| Run No. | $SnCl_4$, mmoles | $SiCl_4$, mmoles | Carbene Complex, mmoles | Olefin, mmoles | | Time, Hours | Product Yield, % |
|---|---|---|---|---|---|---|---|
| 98[a] | 2 | 3 | 0.22 | cis-2-Pentene | 22 | 48 | c |
| 99[b] | 10 | 15 | 1 | 1-Hexene | 1000 | 28 | 16[d] |
| 100[b] | 15 | 15 | 5 | 1-Hexene | 1000 | 48 | 23[d] |
| 101[b] | 20 | 30 | 2 | 1-Decene | 2000 | 120 | 12[d] |
| 102[b] | 50 | 50 | 5 | 1-Tetradecene | 500 | 48 | 30[d] |

[a]Chlorobenzene diluent
[b]Hexane diluent
[c]3-Hexene is present but the yield could not be determined due to glc peak overlap.
[d]Isolated yield.

These runs illustrate the use of embodiment A for the disproportionation of cis-2-pentene to 3-hexene and 2-butene, 1-hexene to 5-decene and ethylene, 1-decene to 9-octadecene and ethylene, and 1-tetradecene to 12-hexacosene and ethylene. The yields in Table IX are isolated yields of the first of the two products listed above for each reaction.

EXAMPLE XI

Embodiment B of the present invention is illustrated for the disproportionation of 1-pentene. This embodiment involves a catalyst system containing a carbene complex, a tin, zirconium, or tungsten halide or tungsten oxyhalide, and a tetraorganogermanium. In each run, 22 mmoles of 1-pentene, 0.22 mmoles of (methoxyphenylcarbene)pentacarbonyltungsten(O), several other components, and chlorobenzene or hexane (9 to 14 ml) were charged to the reactor and the mixtures were stirred at 55° C. The other components and the results are shown in Table X.

TABLE X

| Run No. | Metal Halide, mmoles | Other, mmoles | Time, Hours | 4-Octene Yield, % |
|---|---|---|---|---|
| 103[a] | None | Ge(CH$_3$)$_4$, 2 | 20 | 0 |
| 104[a] | SnCl$_4$, 3 | Ge(CH$_3$)$_4$, 2 | 20 | 71 |
| 105[a] | SnCl$_4$, 3 | Si(CH$_3$)$_4$, 2.2 | 20 | 45 |
| 106[a] | ZrCl$_4$, 3 | Ge(CH$_3$)$_4$, 2 | 19 | 27 |
| 107[a] | ZrCl$_4$, 3 | Si(CH$_3$)$_4$, 2.2 | 18 | 0 |
| 108[b] | WCl$_6$, 0.22 | Ge(CH$_3$)$_4$, 2 | 48 | 30 |
| 109[b] | WCl$_6$, 0.22 | Ge(CH$_3$)$_4$, 2 | 20 | 25 |

[a]Hexane diluent.
[b]Chlorobenzene diluent.

Tetramethylgermanium in combination with the carbene complex does not catalyze the disproportionation of 1-pentene (run 103). However, the presence of tetramethylgermanium with the carbene complex and $SnCl_4$ (run 104), $ZrCl_4$ (run 106), or $WCl_6$ (runs 108 and 109) results in higher yields of 4-octene than in runs in the absence of tetramethylgermanium (Tables I and II). Tetramethylsilane does not show the same beneficial results (runs 105 and 107).

Several control runs were carried out which show that the presence of tetramethylgermanium with a carbene complex and $TiCl_4$, $TiBr_4$, or $GeCl_4$ does not result in an improved yield over runs without the tetramethylgermanium. These runs were carried out as described above in this example for 20 hours at 55° C. The results are shown in Table XI.

TABLE XI

| Run No. | Metal Halide, mmoles | Other, mmoles | Time, Hours | 4-Octene Yield, % |
|---|---|---|---|---|
| 110 | TiCl$_4$, 3 | Ge(CH$_3$)$_4$, 2 | 20 | 38 |
| 111 | TiBr$_4$, 3 | Ge(CH$_3$)$_4$, 2 | 20 | t[a] |
| 112 | GeCl$_4$, 3 | Ge(CH$_3$)$_4$, 2 | 20 | 0 |

[a]t = trace.

EXAMPLE XII

The runs in this example involve embodiment C of the present invention. Embodiment C uses carbon tetrachloride as a component of the catalyst system with carbene complexes and a Group IVa halide. Each run used 22 mmoles of 1-pentene, 0.22 mmoles of (methoxyphenylcarbene)pentacarbonyltungsten(0), various other materials, and hexane (9 to 14 ml) except in run 115 which did not include hexane. Each mixture was stirred at 55° C. The results are presented in Tables XII and XIII. Runs 85 and 11 are included from previous examples for comparison.

TABLE XII

| Run No. | Metal Halide, mmoles | Halide, mmoles | Time, Hours | 4-Octene Yield, % |
|---|---|---|---|---|
| 85 | SiCl$_4$ 20 | None | 24 | 0 |
| 113 | None | CCl$_4$ 0.2 | 96 | 0 |
| 114 | None | CCl$_4$ 3 | 23 | 0 |
| 115 | None | CCl$_4$ 50 | 24 | 16 |
| 116 | SiCl$_4$ 2 | CCl$_4$ 3 | 24 | 31 |
| 11[a] | GeCl$_4$ 2 | None | 20 | 10 |
| 117 | GeCl$_4$ 2 | CCl$_4$ 3 | 20 | 27 |
| 118 | SnCl$_4$ 2 | CCl$_4$ 3 | 20 | 68 |
| 119 | SnCl$_4$ 3 | CCl$_4$ 3 | 72 | 56 |
| 120 | SnCl$_4$ 3 | CCl$_4$ 3 | 1 | t |
|  |  |  | 2 | 9 |
|  |  |  | 20 | 46 |
| 121 | SnCl$_4$ 2 | CCl$_4$ 3 | 3.3 | 19 |
|  |  |  | 4.3 | 23 |
|  |  |  | 21 | 57 |

[a]Reaction temperature = 150° C.

TABLE XIII

| Run No. | Metal Halide, mmoles | Halide, mmoles | Time, Hours | 4-Octene Yield, % |
|---|---|---|---|---|
| 122 | None | CBr$_4$ 3 | 20 | t |
| 123 | SnCl$_4$ 3 | CBr$_4$ 3 | 20 | 43 |
| 124 | None | Cl$_3$CCCl$_3$ 3 | 72 | 47 |
| 125 | SnCl$_4$ 3 | Cl$_3$CCCl$_3$ 3 | 48 | 62 |
| 126 | None | BrCCl$_3$ 3 | 20 | 13 |
| 127 | SnCl$_4$ 3 | BrCCl$_3$ 3 | 20 | 42 |
| 128 | None | Cl$_3$CC=CCl$_2$ $\vert$ Cl  3 | 72 | 2 |

TABLE XIII-continued

| Run No. | Metal Halide, mmoles | Halide, mmoles | Time, Hours | 4-Octene Yield, % |
|---|---|---|---|---|
| 129 | SnCl$_4$  3 | Cl$_3$CC=CCl$_2$ 3<br>    |<br>    Cl | 20 | 9 |
| 130 | None |    O 3<br>   ‖<br>Cl$_3$CCCl$_3$ | 72 | 3 |
| 131 | SnCl$_4$  3 |    O 3<br>   ‖<br>Cl$_3$CCCCl$_3$ | 20 | 3 |
| 132 | GeCl$_4$  3 | Cl$_3$CC=CCl$_2$ 3<br>    |<br>    Cl | 20 | 3 |
| 133 | SiCl$_4$  3 | Cl$_3$CC=CCl$_2$ 3<br>    |<br>    Cl | 19 | t |
| 134 | SiCl$_4$  3 | Cl$_3$CCCl$_3$ 3 | 48 | 44 |
| 135 | WCl$_6$  0.22 | CCl$_4$ 3 | 20 | 0 |

The results in Table XII show that CCl$_4$ in combination with a carbene complex results in olefin disproportionation only at the highest level (run 115). However, CCl$_4$ at low levels in combination with a carbene complex and SiCl$_4$, GeCl$_4$, or SnCl$_4$ result in higher disproportionation yields that runs in the absence of the CCl$_4$.

The control runs in Table XIII show that a variety of other halogenated materials do not give the improved disproportionation yield provided by CCl$_4$. Run 135 shows that CCl$_4$ is not suitable for improving the olefin disproportionation reaction with WCl$_6$ and a carbene complex.

EXAMPLE XIII

This example illustrates embodiment D of the present invention for olefin disproportionation in the presence of a carbene complex, a zirconium halide, and a tetraorganotin. Each run was carried out in hexane (4 to 14 ml) at 55° C. (except run 137) with 22 mmoles of 1-pentene, 0.22 mmoles of (methoxyphenylcarbene)pentacarbonyltungsten(0), and several other components. The results are presented in Table XIV.

TABLE XIV

| Run No. | Metal Halide, mmoles | Sn(CH$_3$)$_4$, mmoles | Time, Hours | 4-Octene Yield, % |
|---|---|---|---|---|
| 136 | None | 2.2 | 96 | 0 |
| 137 | None | 1.1 | a | 0 |
| 138 | ZrCl$_4$  3 | 2 | 18 | 17 |
| 139 | TiCl$_4$  3 | 2 | 20 | 80 |
| 140 | TiCl$_4$  3 | 2 | 20 | 65 |
| 141 | TiCl$_4$  3 | 2 | 20 | 44 |
| 142 | SnCl$_4$  2 | 2 | 20 | 23 |
| 143 | SnCl$_4$  3 | 2 | 20 | 27 |
| 144 | GeCl$_4$  2 | 2 | 20 | 0 |
| 145 | WCl$_6$  0.22 | 2 | 20 | t$^b$ |

$^a$24 hours at room temperature 48 hours at 130° C.
$^b$t = trace

These results show that although tetramethyltin in combination with a carbene complex (runs 136, 137) does not cause olefin disproportionation, the combination of tetramethyltin with a carbene complex and zirconium tetrachloride (run 138) does result in an improved disproportionation yield compared with a similar run in the absence of the tetramethyltin (run 18 of Table I). In contrast to this improvement, tetramethyltin results in either mixed results with TiCl$_4$ (runs 139 to 141) or reduced yields with SnCl$_4$ (runs 142 and 143), GeCl$_4$ (run 144), or WCl$_6$ (run 145) compared with runs in the absence of tetramethyltin (runs in Tables I and II).

EXAMPLE XIV

The disproportionation of 4-penten-1-yl acetate to 1,8-diacetoxy-4-octene and ethylene in the presence of the catalyst system of this invention was demonstrated. In each run, the reaction bottle was charged with 16 mmoles of 4-penten-1-yl acetate (22 mmoles in run 155), (methoxyphenylcarbene)pentacarbonyltungsten(0), a metal halide, and either chlorobenzene or hexane (13 to 19 ml). The mixtures were stirred at 55° C. The quantities and results are shown in Table XV.

TABLE XV

| Run No. | Metal Halide, mmoles | Group | Carbene Complex mmoles | Diluent | Time, Hours | 1,8-Diacetoxy-4-Octene Yield,$^a$ % |
|---|---|---|---|---|---|---|
| 146 | SnCl$_4$ 3.2 | IVa | 0.32 | C$_6$H$_5$Cl | 48 | 33 |
| 147 | SnCl$_4$ 3.2 | IVa | 0.16 | Hexane | 48 | 13 |
| 148 | SnBr$_4$ 2 | IVa | 0.16 | C$_6$H$_5$Cl | 120 | t |
| 149 | WCl$_6$ 0.32 | VIb | 0.16 | C$_6$H$_5$Cl | 120 | 7 |
| 150 | WCl$_6$ 0.16 | VIb | 0.16 | C$_6$H$_5$Cl | 72 | 5 |
| 151 | WOCl$_4$ 0.32 | VIb | 0.16 | Hexane | 120 | 30 |
| 152 | WBr$_5$ 0.44 | VIb | 0.16 | C$_6$H$_5$Cl | 120 | 0 |
| 153 | MoCl$_5$ 0.32 | VIb | 0.16 | Hexane | 168 | 3 |
| 154 | MoOCl$_4$ 0.44 | VIb | 0.22 | Hexane | 120 | 2 |
| 155 | TiCl$_4$ 3 | IVb | 0.22 | Hexane | 20 | 0 |
| 156 | ReCl$_5$ 0.32 | VIb | 0.16 | C$_6$H$_5$Cl | 20 | 1 |
| 157 | SnF$_4$ 1.6 | IVa | 0.16 | C$_6$H$_5$Cl | 48 | 0 |

$^a$t = trace

These results demonstrate the process of this invention for the disproportionation of an unsaturated ester in the presence of SnCl$_4$, WCl$_6$, WOCl$_4$, MoCl$_5$, MoOCl$_4$, or ReCl$_5$ and a carbene complex. The metal bromides (runs 148 and 152) and fluorides (run 157) are ineffective as catalyst components. Run 155 suggests that TiCl$_4$ is not an effective catalyst component with esters.

EXAMPLE XV

Several more runs were carried out with other unsaturated esters to demonstrate disproportionation with the catalyst system of the present invention. In the first group, methyl 10-undecenoate was disproportionated to ethylene and dimethyl 10-eicosen-1,20-dioate. In each run, 20 mmoles (50 mmoles in run 162) of methyl 10-undecenoate, 0.2 or 0.22 mmoles (0.5 mmoles in run 162) of (methoxyphenylcarbene)pentacrbonyltungsten(0), one or more metal chlorides, and chlorobenzene (hexane in run 161) 14 to 18 ml (25 ml in run 162 were utilized). All reactions were carried out at 55° C. The results in Table XVI are expressed in terms of the yield of dimethyl 10-eicosen-1,20-dioate.

TABLE XVI

| Run No. | Metal Halide, mmoles | | Metal Halide, mmoles | | Time, Hours | Product Yield,[a] % |
|---|---|---|---|---|---|---|
| 158 | SnCl$_4$ | 4 | None | | 48 | 46 |
| 159 | SnCl$_4$ | 2 | None | | 48 | 40 |
| 160 | SnCl$_4$ | 2 | None | | 20 | 22 |
| 161 | SnCl$_4$ | 2 | None | | 72 | 16 |
| 162 | WCl$_6$ | 0.5 | None | | 96 | 16 |
| 163 | WOCl$_4$ | 0.44 | None | | 72 | 5 |
| 164 | SnCl$_4$ | 0.22 | WCl$_6$ | 0.2 | 72 | 24 |
| 165 | SnCl$_4$ | 2 | WCl$_6$ | 0.1 | 72 | 20 |
| 166 | SnCl$_4$ | 2 | WCl$_6$ | 0.2 | 72 | 10 |
| 167 | SnCl$_4$ | 2 | GeCl$_4$ | 3 | 96 | 28 |

[a]Dimethyl 10-eicosen-1,20-dioate

Although the results in Table XVI are variable, they show that the combination of one or two metal chlorides or metal oxychlorides in combination with a carbene complex catalyzes the disproportionation of methyl 10-undecenoate.

The disproportionation of methyl oleate to 9-octadecene and dimethyl 9-octadecen-1,8-dioate was also carried out. Both runs used 22 mmoles of methyl oleate, 0.22 mmoles of (methoxyphenylcarbene)pentacarbonyltungsten(0), SnCl$_4$ (2 or 2.2 mmoles), and 14.4 ml of chlorobenzene and were carried out at 55° C. In runs 168 and 169, the disproportionation of methyl oleate occurred. The yields are presented in Table XVII.

TABLE XVII

| Run No. | Metal Halide, mmoles | | Time, Hours | Diester Yield,[a] % | 9-Octadecene Yield, % |
|---|---|---|---|---|---|
| 168 | SnCl$_4$ | 2.2 | 20 | 3 | 4 |
| 169 | SnCl$_4$ | 2 | 72 | 11 | 11 |

[a]Dimethyl-9-octadecen-1,18-dioate

EXAMPLE XVI

The co-disproportionation of cyclopentene with 4-penten-1-yl acetate in the presence of metal halides is demonstrated in this example. In each run, the reaction bottle was charged with cyclopentene (from 14 to 22 mmoles), 4-penten-1-yl acetate, (from 16 to 22 mmoles), a metal halide, (methoxyphenylcarbene)pentacarbonyltungsten(0), and chlorobenzene or hexane (6 to 24 ml). Each reaction was carried out at 55° C. Products identified from this reaction include 4,9-decadien-1-yl acetate (DDA), 1,8-diacetoxy-4-octene (DAO), and 4,9,14-pentadecatrien-1-yl acetate. The results are shown in Table XVIII.

TABLE XVIII

| Run No. | Metal Halide, mmoles | | Carbene Complex mmoles | Time, Hours | DDA Yield, % | DAO[a] Yield, % |
|---|---|---|---|---|---|---|
| 170 | SnCl$_4$ | 1.6 | 0.16 | 96 | 15 | 16 |
| 171 | SnCl$_4$ | 4 | 0.44 | 72 | 17 | ND |
| 172 | SnCl$_4$ | 2 | 0.15 | 72 | 4 | ND |
| 173 | WCl$_6$ | 0.16 | 0.16 | 96 | 17 | 9 |
| 174 | WCl$_6$ | 0.22 | 0.22 | 20 | 14 | ND |
| 175 | WCl$_6$ | 1 | 0.22 | 24 | 10 | ND |
| 176 | MoCl$_5$ | 1 | 0.22 | 24 | 10 | ND |
| 177 | MoBr$_5$ | 0.22 | 0.22 | 48 | 0 | ND |
| 178 | VCl$_4$ | 2.2 | 0.22 | 20 | 0 | 0 |
| 179 | ZrCl$_4$ | 2.2 | 0.22 | 20 | 9 | ND |
| 180 | TaCl$_5$ | 0.44 | 0.22 | 20 | 14 | ND |
| 181 | TaCl$_5$ | 0.44 | 0.44 | 20 | 3 | ND |
| 182 | ReCl$_5$ | 1 | 0.22 | 20 | 14 | ND |
| 183 | ReCl$_5$ | 0.44 | 0.22 | 20 | 7 | 2 |
| 184 | ReCl$_5$ | 2.2 | 0.22 | 48 | 7 | ND |
| 185 | FeCl$_3$ | 0.43 | 0.22 | 20 | 2 | ND |

[a]ND = Not determined.

These results show that the combination of a carbene complex and a metal chloride are suitable for the co-disproportionation of cyclopentene with 4-penten-1-yl acetate. No disproportionation was observed with MoBr$_5$ or with VCl$_4$ at a level (mole ratio of VCl$_4$ to carbene complex of 10/1) above the range that is known to be effective.

EXAMPLE XVII

Several more runs were carried out to determine which functional groups can be successfully disproportionated with the catalyst system of present invention and the critical distances between the olefinic group and the functional group. In each run, the olefin (22 mmoles except in run 192 where 30 mmoles of each olefin was used), (methoxyphenylcarbene)pentacarbonyltungsten(0) (0.22 to 0.3 mmoles), a metal chloride, and either hexane or chlorobenzene (9 to 14 ml) were charged to the reaction bottle and the mixture was stirred at 55° C. Table XIX presents the results.

TABLE XIX

| Run No. | Metal Halide, mmoles | | Olefin | Time, Hours | Product Yield, % |
|---|---|---|---|---|---|
| 186 | SnCl$_4$ | 2 | Allyl Acetate | 20 | 0 |
| 187 | SnCl$_4$ | 2 | Allyl Alcohol | 96 | 0 |
| 188 | WCl$_6$ | 0.22 | Allyl Chloride | 48 | 0 |
| 189 | SnCl$_4$ | 0.22 | Allyloxytrimethylsilane | 24 | 0 |
| 190 | TiCl$_4$ | 3 | Allyloxytrimethylsilane | 20 | 0 |
| 191 | SnCl$_4$ | 3 | Cyclopentene and 3-Butene nitrile | 24 | 0 |
| 192 | WCl$_6$ | 0.22 | 5-Hexen-2-one | 72 | 0 |
| 193 | SnCl$_4$ | 2.2 | 5-Chloro-1-pentene | 24 | 17[a] |
| | | | | 48 | 26[a] |
| 194 | SnCl$_4$ | 4 | Ethyl Oleyl Ether | 20 | 10[b] |
| | | | | | 11[c] |

[a]1,8-Dichloro-4-octene
[b]9-Octadecene [c]1,18-Diethoxy-9-octadecene

These results show that olefins containing ester (run 186), alcohol (run 187), chloride (run 188), trimethylsilyloxy (runs 189 and 190), or nitrile (run 191) groups located only one carbon atom from the olefinic group do not undergo disproportionation with the catalyst system of the present invention. Unsaturated ketones (run 192) are not suitable as disproportionation substrates. Unsaturated chlorides (run 193) and unsaturated ethers (run 194) with at least two carbon atoms between the olefinic group and the chloride or ether were found to undergo disproportionation in the presence of the catalyst system of this invention.

The results in this example show clearly the difference in behavior between the prior art catalyst systems and the catalyst system of this invention. For example, the disproportionation catalyst of U.S. Pat. No. 3,974,196 was capable of catalyzing the disproportionation of allyl acetate, 3-butenenitrile, and 5-hexen-2-one, while the present catalyst system was shown in Table XIX to be essentially inert towards these compounds. Therefore, the present catalyst system is more selective towards functional olefins than prior art catalysts.

EXAMPLE XVIII

Embodiment A of this invention can be utilized for the disproportionation of unsaturated esters. Embodiment A uses a carbene complex, a germanium, tin, or lead tetrahalide, and silicon tetrahalide as the catalyst system. Table XX presents the results from runs in which 4-penten-1-yl acetate (16 mmoles) was disproportionated to ethylene and 1,8-diacetoxy-4-octene in the presence of (methoxyphenylcarbene)pentacarbonyltungsten(0), $SnCl_4$, $SiCl_4$ and a diluent at 55° C.

TABLE XX

| Run No. | $SnCl_4$, mmoles | $SiCl_4$, mmoles | Carbene Complex mmoles | Diluent | Time, Hours | Product Yield,[a] % |
|---|---|---|---|---|---|---|
| 195 | 3.2 | 6 | 0.32 | $C_6H_5Cl$ | 24 | 42 |
| 196 | 1.6 | 3 | 0.16 | $C_6H_5Cl$ | 120 | 42 |
| 197 | 1.6 | 3 | 0.16 | Hexane | 48 | 33 |
| 198 | 1.6 | 3 | 0.16 | $C_6H_5Cl$ | 1 | 0.3 |
|  |  |  |  |  | 2 | 1 |
|  |  |  |  |  | 5 | 14 |
|  |  |  |  |  | 24 | 40 |
|  |  |  |  |  | 48 | 39 |
| 199 | 1.6 | 3 | 0.16 | $C_6H_5NO_2$ | 18 | 0 |
| 200 | 1.6 | 3 | 0.16 | $CH_3CN$ | 20 | 0 |

[a]1,8-Diacetoxy-4-octene

The yields of 1,8-diacetoxy-4-octene were increased when compared with the yields in similar runs in Example XIV in the absence of $SiCl_4$. The use of nitrobenzene or acetonitrile as diluents (runs 199 and 200) was found to prevent disproportionation.

EXAMPLE XIX

Several other runs were carried out to demonstrate the use of embodiment A for the disproportionation of unsaturated esters. In run 201, 21 mmoles of methyl oleate, 0.22 mmoles of (methoxyphenylcarbene)pentacarbonyltungsten(0), 2.2 mmoles of $SnCl_4$, and 2.2 mmoles of $SiCl_4$ in about 18 ml of chlorobenzene were stirred at 55° C. for 72 hours. The reaction product mixture contained a 16% yield of 9-octadecene and about a 10% yield of dimethyl 9-octadecen-1,18-dioate. The yield of 9-octadecene is increased over the yield of run 168 which did not use $SiCl_4$.

In run 202, methyl oleate and ethylene were co-disproportionated by contacting 22 mmoles of methyl oleate with ethylene (30 psi), 0.22 mmoles of (methoxyphenylcarbene)pentacarbonyltungsten(0), 2.2 mmoles of $SnCl_4$, and 3 mmoles of $SiCl_4$ in about 16 ml of hexane at 55° C. for 72 hours. An analysis of the reaction product mixture showed that 1-decene and methyl 9-decen-1-oate were present in yield of 13% each.

Numerous runs were carried out to investigate the disproportionation of methyl 10-undecenoate to ethylene and dimethyl 10-eicosen-1,20-dioate using embodiment A of this invention. While the yield varied considerably from run to run, the average yield of dimethyl 10-eicosen-1,20-dioate from 7 runs using a mixture of methyl 10-undecenoate, (methoxyphenylcarbene)pentacarbonyltungsten(0), $SnCl_4$, and $SiCl_4$ in a mole ratio of 100/1/10/15 in chlorobenzene at 55° C. for 3 to 6 days was 27%. The average yield of dimethyl 10-eicosen-1,20-dioate in a series of 6 runs using the same reagents and conditions except for the absence of $SiCl_4$ was 23%. Therefore, the presence of $SiCl_4$ increases the disproportionation product yield.

EXAMPLE XX

Embodiment A of this invention was utilized with several other functional olefins. In each run, 20 to 22 mmoles of the olefin, 0.2 or 0.22 mmoles of (methoxyphenylcarbene)pentacarbonyltungsten(0), $SnCl_4$, and $SiCl_4$ in hexane or chlorobenzene were stirred at 55° C. The reaction product mixtures were analyzed by glc and the results are presented in Table XXI.

TABLE XXI

| Run No. | $SnCl_4$, mmoles | $SiCl_4$, mmoles | Olefin | Time, Hours | Metathesis Product Yield, % |
|---|---|---|---|---|---|
| 203 | 2 | 3 | 6-Chloro-1-hexene | 48 | 60[a] |
| 204 | 2.2 | 3 | 5-Chloro-1-pentene | 96 | 49[b] |
| 205 | 2 | 3 | 4-Chloro-1-butene | 48 | 12[c] |
| 206 | 2 | 4 | Ethyl Oleyl Ether | 96 | 9[d] |
|  |  |  |  |  | 12[e] |
| 207 | 2.2 | 3 | Allyl Chloride | 48 | 0 |
| 208 | 2.2 | 3 | Allyl Acetate | 20 | 0 |
| 209 | 2 | 3 | Allyl Ethyl Ether | 96 | 0 |

[a]1,10-Dichloro-5-decene
[b]1,8-Dichloro-4-octene
[c]1,6-Dichloro-3-hexene
[d]9-Octadecene
[e]1,8-Ethoxy-9-octadecene The catalyst system used in this example caused the disproportionation of a series of unsaturated chlorides with decreasing yields as the distance between the chloride and the olefinic group decreased (runs 203, 204, 205). The yield in run 204 was significantly increased over the corresponding run (run 193 of Example XVII) without the presence of $SiCl_4$. Ethyl oleyl ether (run 206) was disproportionated in slightly higher yields than the corresponding run (run 194 in Example XVII) in the absence of $SiCl_4$. Functional olefins having a chloride, ester, or ether located only one carbon atom from the olefinic group were inactive for disproportionation (runs 207 to 209).

Attempts to use (phenylthiophenylcarbene)pentacarbonyltungsten(0) in the catalyst system of embodiment A with several unsaturated esters yielded essentially no disproportionation. This suggests that this carbene complex is not suitable for use in embodiment A for functional olefins under the reaction conditions used. Also found to be unsuitable for use in embodiment A were (methoxymethylcarbene)pentacarbonyltungsten(0), (methoxyphenylcarbene)pentacarbonylchromium(0), and (methylthiophenylcarbene)pentacarbonyltungsten(0).

As will be evident to those skilled in the art, many variations and modifications of the present invention can be practiced in view of the foregoing disclosure without departing from the spirit and scope thereof.

What is claimed is:

1. A catalyst for the disproportionation of olefins comprising:
   (1) at least one inorganic metal compound component selected from a chloride or bromide of a metal of Group IVa (including germanium), IVb, Vb, VIb, VIIb, VIII, or Ib of the Periodic Table, or an oxychloride or oxybromide of molybdenum, tungsten, vanadium, or chromium; wherein if the metal is vanadium it is in an oxidation state of either 4 or its highest stable common ionic oxidation state, if the metal is molybdenum, tungsten, or rhenium, it is in an oxidation state of either 5 or its highest stable common ionic oxidation state, and if the metal is other than vanadium, molybdenum, tungsten, or rhenium, the metal is in its highest stable common ionic oxidation state; and
   (2) at least one neutral carbene complex having the general formula

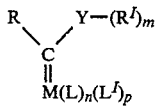

wherein R is an alkyl or cycloalkyl radical containing 1 to 10 carbon atoms, an aryl or substituted aryl radical containing 6 to 30 atoms, wherein the substituted radicals have one or more substituents each of which is the same or different and is a halide, alkoxide, or alkyl radical containing 1 to 20 carbon atoms; $R^I$ is an alkyl, cycloalkyl, aryl, substituted aryl, triarylsilyl or trialkylsilyl radical containing 1 to 30 carbon atoms, and the aryl substituents are as described for R; M is tungsten or rhenium when component (1) does not contain titanium or M is chromium when component (1) does contain titanium; Y is oxygen, sulfur, selenium, nitrogen or phosphorus; each L is a neutral ligand individually selected from CO, NO, $PR^I_3$, $PCl_3$, $PF_3$, and pyridine, where $R^I$ is as defined above; $L^I$ is cyclopentadienyl; p is 0 or 1; n is 5 when p is 0 and n is 2 when p is 1; and m is 2 when Y is nitrogen or phosphorus and m is 1 when Y is oxygen, sulfur or selenium; wherein the molar ratio of component (1) to component (2) is in the range of 1:1 to 500:1.

2. A catalyst according to claim 1, wherein component (1) is at least one metal compound selected from germanium tetrachloride, tin tetrachloride, tin tetrabromide, lead tetrachloride, zirconium tetrachloride, hafnium tetrachloride, vanadium tetrachloride, vanadium oxytrichloride, niobium pentachloride, tantalum pentachloride, chromium trichloride, molybdenum pentachloride, molybdenum pentabromide, molybdenum oxytetrachloride, tungsten hexachloride, tungsten pentabromide, tungsten oxytetrachloride, manganese trichloride, rhenium pentachloride, iron trichloride, iron tribromide, cobalt trichloride, nickel(II) bromide, ruthenium trichloride, rhodium trichloride, palladium dichloride, osmium trichloride, iridium tetrachloride, platinum tetrachloride, copper(II) chloride, copper(II) bromide, silver chloride, and gold(III) chloride.

3. A catalyst according to claim 2 wherein said carbene complex component is selected from the group consisting of (methoxyphenylcarbene)pentacarbonyltungsten(0), (p-chlorophenylmethoxycarbene)pentacarbonyltungsten(0), (p-methylphenylmethoxycarbene)pentacarbonyltungsten(0), (p-methoxyphenylmethoxycarbene)pentacarbonyltungsten(0), (phenoxyphenylcarbene)pentacarbonyltungsten(0), (cyclohexyloxyphenylcarbene)pentacarbonyltungsten(0), (butoxyphenylcarbene)pentacarbonyltungsten(0), (octyloxyphenylcarbene)pentacarbonyltungsten(0), (hexadecyloxyphenylcarbene)pentacarbonyltungsten(0), (eicosyloxyphenylcarbene)pentacarbonyltungsten(0), (phenyltrimethylsilyloxycarbene)pentacarbonyltungsten(0), (phenyltriphenylsilyloxycarbene)pentacarbonyltungsten(0), (methylthiophenylcarbene)pentacarbonyltungsten(0), (dimethylaminophenylcarbene)pentacarbonyltungsten(0), (methoxyphenylcarbene)pentanitrosyltungsten(0), (methoxyphenylcarbene)$\eta^5$-cyclopentadienyldicarbonyl rhenium(I), (methoxyphenylcarbene)tetracarbonyl(triphenylphosphine)tungsten(0), and (methoxyphenylcarbene)pentacarbonylchromium(0).

4. A catalyst according to claim 3 wherein said metal compound component is selected from the group consisting of tin tetrachloride, tin tetrabromide, germanium tetrachloride, germanium tetrabromide, lead tetrachloride, and lead tetrabromide and wherein said catalyst composition includes a promoting amount of silicon tetrachloride or silicon tetrabromide.

5. A catalyst according to claim 3 wherein said metal compound component is selected from the group consisting of tin tetrachloride, tin tetrabrmode, zirconium tetrabromide, tungsten hexachloride, tungsten hexabromide, tungsten pentachloride, tungsten oxytetrabromide, tungsten oxytetrachloride, and tungsten pentabromide and wherein said catalyst composition includes a promoting amount of at least one tetraorganogermanium compound of the formula $GeR^{II}_4$ wherein $R^{II}$ is an alkyl, aryl, or alkaryl radical containing from 1 to 10 carbon atoms per radical.

6. A catalyst according to claim 3 wherein said metal compound component is selected from the tetrachlorides and tetrabromides of germanium, tin, and lead and wherein said catalyst composition includes a promoting amount of carbon tetrachloride.

7. A catalyst according to claim 3 wherein said metal compound component is selected from the group of zirconium tetrachloride and zirconium tetrabromide and wherein said catalyst composition further includes a promoting amount of at least one tetraorganotin compound of the formula $SnR^{II}_4$ wherein $R^{II}$ is an alkyl, aryl, or alkaryl radical containing from 1 to 10 carbon atoms per radical.

8. A catalyst for the disproportionation of olefins comprising effective amounts of
   (1) silicon tetrachloride,
   (2) at least one neutral carbene complex having the general formula

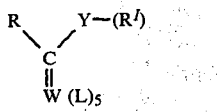

wherein R is selected from the group consisting of alkyl or cycloalkyl radicals containing 1 to 10 carbon per radical and aryl or substituted aryl radicals containing 6 to 30 carbon atoms per radical wherein the substituted radicals can have one or more substitutents each of which can be the same or different and selected from the group consisting of halides, alkoxides, and alkyl radicals containing 1 to 20 carbon atoms per radical; wherein $R^I$ is selected from the group consisting of alkyl, cycloalkyl; aryl, substituted aryl, triarylsilyl, and trialkylsilyl radicals containing 1 to 30 carbon atoms per radical and wherein the aryl substituents are as described for R, Y is O or S, L is CO or NO, and R and R arenot both aryl or substituted aryl when Y is S and nonfunctional olefin reactant is employed; and (3) a promoting amount of carbon tetrachloride, wherein the molar ratio of said silicon tetrachloride to said carbene complex component is in the range of about 1/1 to about 500/1 and the molar ratio of said carbon tetrachloride to said silicon tetrachloride is in the range of about 0.1/1 to about 200/1.

9. A catalyst according to claim 8 wherein L is CO.

10. A catalyst according to claim 9 wherein said carbene complex is (methoxyphenylcarbene)pentacarbonyltungsten(0).

* * * * *